United States Patent
Favara et al.

(10) Patent No.: US 11,026,886 B2
(45) Date of Patent: *Jun. 8, 2021

(54) BLEND COMPOSITIONS FOR ORAL ADMINISTRATION AS A RAPIDLY DISSOLVING POWDER AND/OR SUSPENSION

(71) Applicant: MARENDA PHARMACEUTICALS LLC, Clearwater, FL (US)

(72) Inventors: Andrew Favara, New Egypt, NJ (US); Marc Karetny, Chula Vista, CA (US)

(73) Assignee: Marenda Pharmaceuticals LLC, Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/591,427

(22) Filed: Oct. 2, 2019

(65) Prior Publication Data

US 2020/0170943 A1 Jun. 4, 2020

Related U.S. Application Data

(63) Continuation of application No. 15/838,254, filed on Dec. 11, 2017, now Pat. No. 10,471,006.

(60) Provisional application No. 62/529,170, filed on Jul. 6, 2017.

(51) Int. Cl.
| | |
|---|---|
| *A61K 9/00* | (2006.01) |
| *A61K 9/08* | (2006.01) |
| *A61K 9/20* | (2006.01) |
| *A61K 31/192* | (2006.01) |
| *A61P 29/00* | (2006.01) |
| *A61K 47/12* | (2006.01) |
| *A61K 47/26* | (2006.01) |
| *A61K 47/36* | (2006.01) |
| *A61K 47/44* | (2017.01) |

(52) U.S. Cl.
CPC ............ *A61K 9/0056* (2013.01); *A61K 9/009* (2013.01); *A61K 9/08* (2013.01); *A61K 9/2018* (2013.01); *A61K 9/2068* (2013.01); *A61K 31/192* (2013.01); *A61K 47/12* (2013.01); *A61K 47/26* (2013.01); *A61K 47/36* (2013.01); *A61K 47/44* (2013.01); *A61P 29/00* (2018.01)

(58) Field of Classification Search
CPC .. A61K 9/0056; A61K 9/2018; A61K 31/192; A61K 9/2068; A61K 9/08; A61K 9/009; A61K 47/26; A61K 47/12; A61K 47/36; A61K 47/44; A61P 29/00

See application file for complete search history.

(56) References Cited

U.S. PATENT DOCUMENTS

| | | | |
|---|---|---|---|
| 5,405,616 A | 4/1995 | Wunderlich et al. | |
| 7,001,892 B1 | 2/2006 | Chmielewski et al. | |
| 9,392,814 B2 | 7/2016 | Singer | |
| 9,399,020 B2 | 7/2016 | Deshpande et al. | |
| 10,471,006 B2 * | 11/2019 | Favara | A61K 9/009 |
| 2003/0232097 A1 | 12/2003 | Radhakrishnan et al. | |
| 2006/0068064 A1 | 3/2006 | Richards | |
| 2007/0170196 A1 | 7/2007 | Libohova I, et al. | |
| 2011/0038940 A1 | 2/2011 | Grizeau | |
| 2011/0280851 A1 | 11/2011 | Herzlinger et al. | |
| 2012/0141503 A1 | 6/2012 | Frenken et al. | |
| 2013/0064893 A1 * | 3/2013 | Yadav | A61P 25/08 424/474 |
| 2013/0331461 A1 | 12/2013 | Zimmeck et al. | |
| 2015/0359743 A1 | 12/2015 | Davis et al. | |
| 2016/0228371 A1 | 8/2016 | Schultz et al. | |

FOREIGN PATENT DOCUMENTS

| | | |
|---|---|---|
| WO | WO-9410994 A1 | 5/1994 |
| WO | WO-2013183062 A2 | 12/2013 |
| WO | WO-2019009927 A1 | 1/2019 |

OTHER PUBLICATIONS

Coupland et al.: Physical Approaches to Masking Bitter Taste: Lessons from Food and Pharmaceuticals. Pharmaceutical Research. 31: 2921-2939 (2014).
De Klerk et al.: Patient compliance in rheumatoid arthritis, polymyalgia rheumatica, and gout. J Rheumatol 30(1): 44-54 (2003).
Elworthy et al.: The Physical Chemistry of Lecithins. J Pharmacy Pharmacol 8: 1001-1018 (1956).
Fass et al.: Pharmacokinetic comparison of orally-disintegrating metoclopramide with conventional metoclopramide tablet formulation in healthy volunteers. Aliment Pharmacol Ther 30: 301-306 (2009).
Kanabar, D.J.: A clinical and safety review of paracetamol and ibuprofen in children. Inflammopharmacol 25(1): 1-9 (2017).
Kelley et al.: Ibuprofen does not increase bleeding risk in plastic surgery: a systematic review and meta-analysis. Plast Reconstr Surg 137(4): 1309-1316 (2016).
Khalifa et al.: Use of ibuprofen sustained release for treating osteoarthritic pain: findings from 15 general medical practices in Egypt. Rheumatology: Research and Reviews 6: 49-56 (2014).
Mennella et al.: The Bad Taste of Medicines: Overview of Basic Research on Bitter Taste. Clin Ther 35(8): 1225-1246 (2013).

(Continued)

*Primary Examiner* — Robert A Wax
*Assistant Examiner* — Quanglong N Truong
(74) *Attorney, Agent, or Firm* — Wilson Sonsini Goodrich & Rosati

(57) ABSTRACT

Disclosed is a dry powder oral formulation that includes an active pharmaceutical ingredient (API), a lecithin powder, a galactomannan, one or more sweetening agents, one or more flavoring agents and an organic acid in a pharmaceutically acceptable preparation. Also disclosed are an excipient composition in absence of an API and methods of making and using the formulations and compositions. Also disclosed is a chewable, swallowable, and/or orally disintegrating tablet comprising an active pharmaceutical ingredient (API), a lecithin powder, a galactomannan, one or more sweetening agents, one or more flavoring agents and an organic acid in a pharmaceutically acceptable preparation.

20 Claims, No Drawings

(56) References Cited

OTHER PUBLICATIONS

PCT/US2017/064281 International Search Report and Written Opinion completed on Jan. 23, 2018.
Rainsford, K.D.: Ibuprofen: pharmacology, efficacy and safety. Inflammopharmacology. 7: 275-342 (2009).
Rockwell et al.: Ibuprofen in acute-care therapy. Ann Surg. 211(1): 78-83 (1990).
Savjani et al.: Drug Solubility: Importance and Enhancement Techniques. ISRN Pharmaceutics. 2012: 1-10 (2012).
Shin et al.: Pharmacokinetic and pharmacodynamic evaluation according to absorption differences in three formulations of ibuprofen. Drug Des Devel Ther. 11: 135--141 (2017).
U.S. Appl. No. 15/838,254 Final Office Action dated Dec. 11, 2018.
U.S. Appl. No. 15/838,254 Office Action dated Jun. 1, 2018.
Walsh et al.: Playing hide and seek with poorly tasting paediatric medicines: Do not forget the excipients. Advanced Drug Delivery Reviews 73: 14-33 (2014).

\* cited by examiner

BLEND COMPOSITIONS FOR ORAL ADMINISTRATION AS A RAPIDLY DISSOLVING POWDER AND/OR SUSPENSION

CROSS-REFERENCE TO RELATED APPLICATIONS

This application is a continuation of U.S. application Ser. No. 15/838,254 filed Dec. 11, 2017, which claims priority from U.S. Provisional Application Ser. No. 62/529,170 filed on Jul. 6, 2017, which is incorporated herein by reference in its entirety.

FIELD

The present invention relates to pharmaceutically acceptable formulations of orally administered substances, and more particularly to formulations for orally administering substances, the individual formulations being administrable in either a dry powder form or with a small quantity of water (as preferred by the subject), and to methods for preparation and administering the substances.

INTRODUCTION

Patient acceptance of medications, often referred to as patient adherence, has been reported to average 50% in developing countries around the world (1). Although a number of factors may contribute to the 50% lack of adherence, characteristics of the drug formulation may be of particular importance. For example, oral tablet formulations can sometimes cause dysphasia and/or nausea and vomiting in patients (2). Further, unpleasant taste may be a challenge in administering a medicine particularly for children (3, 4).

Ibuprofen is a commonly used non-steroidal anti-inflammatory drug (NSAID) with multiple beneficial effects including pain relief and reduction of inflammation and fever. (5, 6). Nevertheless, patient adherence may be a challenge in treatment with ibuprofen as well as other NSAIDs (7, 8).

Additionally, formulations which are administrable both in dry powder form and in suspension by adding a minimum quantity of water to dissolve the dry powder are not available on the market. Powder, solution, and suspension dosage forms typically utilize a different set of excipients to achieve acceptable physical properties. For a powder, excipients are chosen on the basis of achieving acceptable physical properties such as flow, density, and compactability. For a solution and suspension dosage forms, excipients are chosen on the basis of achieving acceptable properties such as solubility, suspendability, dispersability, and viscosity. For flavored powders, solutions, and suspensions, the type and concentration of sweeteners and flavors are typically different since the sensory perception of flavor and texture would be different when consuming a powder versus a liquid dosage form. Also, taste masking of active pharmaceutical ingredients (API) are typically dependent on type, concentration, and processing method (i.e., API coating, granule coating, etc.) of excipients.

Therefore, what is needed is a formulation which is administrable both in dry powder form and in suspension by adding a minimum quantity of water to dissolve the dry powder.

SUMMARY

Accordingly, the inventors herein have succeeded in devising formulations that can be administered either as a dry powder or in a small quantity of water. The new formulations provide improved taste and mouthfeel to facilitate ease of administration and patient adherence.

Thus, in various embodiments, the present invention is directed to dry-powder oral formulations that include an active pharmaceutical ingredient (API), a lecithin powder, a galactomannan, one or more sweetening agents, one or more flavoring agents and an organic acid in a pharmaceutically acceptable preparation. In various embodiments, the dry-powder formulation includes ibuprofen; sunflower lecithin powder; guar gum; xylitol and isomalt; cherry, strawberry and raspberry flavorings, grape flavoring, orange flavoring, other fruit flavors, and citric acid, malic acid, fumaric acid, or any other acidulants, and combinations of any of the following, in a pharmaceutically acceptable preparation. In various aspects, the formulation solubility or dispersability in water is no more than about 0.5 w/v. In various aspects, the formulation or an aqueous solution or dispersion thereof is in a unit dosage form in a container selected from the group consisting of a blister foil pack, stick pack, sachet, pouch, bottle, orally disintegrating tablet, dispersible tablet, capsule, powder in a capsule, and spheres in a capsule. In various aspects, the unit dosage form of ibuprofen is in a quantity of about 50, about 100, about 200, about 400, about 600 or about 800 mg.

In various other embodiments, the present invention is directed to a method of administering an API. The method includes providing a dry-powder oral formulation of the API, a lecithin powder, a galactomannan, one or more sweetening agents, one or more flavoring agents and an organic acid in a pharmaceutically acceptable preparation. In various embodiments, the dry-powder formulation includes ibuprofen; sunflower lecithin powder; guar gum; xylitol and isomalt; cherry, strawberry and raspberry flavorings and citric acid in a pharmaceutically acceptable preparation. In various aspects, the formulation solubility or dispersability in water is no more than about 0.5 w/v. In various aspects, the formulation or an aqueous solution or dispersion thereof is in a unit dosage form in a container selected from the group consisting of a blister foil pack, stick pack, sachet, pouch, orally disintegrating tablet, dispersible tablet and capsule. In various aspects, the unit dosage form of ibuprofen is in a quantity of about 50, about 100, about 200, about 400, about 600, or about 800 mg.

Various other embodiments are directed to a method of preparing a dry powder oral formulation of an API. The method includes combining, in any order, an API, a lecithin powder, a galactomannan, one or more sweetening agents, one or more flavoring agents and an organic acid in a pharmaceutically acceptable preparation. In various embodiments, the dry-powder formulation includes ibuprofen; sunflower lecithin powder; guar gum; xylitol and isomalt; cherry, strawberry and raspberry flavorings and citric acid in a pharmaceutically acceptable preparation. In various aspects, the formulation solubility or dispersability in water is no more than about 0.5 w/v. In various aspects, the formulation or an aqueous solution or dispersion thereof is in a unit dosage form in a container selected from the group consisting of a blister foil pack, stick pack, sachet, pouch, orally disintegrating tablet, dispersible tablet and capsule. In various aspects, the unit dosage form of ibuprofen is in a quantity of about 50, about 100, about 200, about 400, about 600 or about 800 mg.

In various other embodiments, the present invention is directed to an excipient composition for combining with an API to produce a drug or nutraceutical composition. The composition includes a lecithin powder, a galactomannan, one or more sweetening agents, one or more flavoring agents and an organic acid in a preparation that when combined with an API produces a pharmaceutically acceptable preparation. In various embodiments, the excipient composition includes a sunflower lecithin powder; guar gum; xylitol and isomalt; cherry, strawberry and, raspberry flavorings and citric acid.

In various other embodiments, the present invention is directed to a dry powder formulation or an aqueous solution or dispersion thereof as described above comprised within a unit dosage form in a container selected from the group consisting of a blister foil pack, stick pack, sachet, pouch, bottle, orally disintegrating tablet, dispersible tablet, powder in a capsule, spheres in a capsule, and capsule.

In yet other embodiments, the present invention is directed to a chewable, swallowable, and/or orally disintegrating tablet comprising an active pharmaceutical ingredient (API), a lecithin powder, a galactomannan, one or more sweetening agents, one or more flavoring agents and an organic acid in a pharmaceutically acceptable preparation.

These and other features, aspects and advantages of the present teachings will become better understood with reference to the following description, examples and appended claims.

DRAWINGS

No drawings are submitted with this application.

DETAILED DESCRIPTION

The present invention is directed to formulations for orally administering substances in a dry powder form or with a small quantity of water and to methods for preparing and administering the formulations.

As used herein, the following terms are defined with the following meanings, unless explicitly stated otherwise.

The term "about" when used before a numerical designation, e.g., pH, temperature, quantity, concentration, and molecular weight, including range, indicates approximations which may vary by ±5%, ±1%, or ±0.1%.

As used in the specification and claims, the singular form "a", "an" and "the" include plural references unless the context clearly dictates otherwise. For example, the term "a pharmaceutically acceptable carrier" may include a plurality of pharmaceutically acceptable carriers, including mixtures thereof.

The term "and/or" is intended to mean either or both of two components of the invention.

The term "subject," "individual" or "patient" is used interchangeably herein, and refers to a human.

The term "device," as used herein, refers to an apparatus or system capable of delivering a drug to patient in need thereof.

The term "in need of treatment" and the term "in need thereof" when referring to treatment are used interchangeably and refer to a judgment made by a caregiver, e.g. physician, nurse, nurse practitioner, that a patient will benefit from treatment.

The term "pharmaceutically acceptable," as used herein, refers to a component of a pharmaceutical composition that is compatible with the other ingredients of the formulation and not overly deleterious to the recipient thereof.

The term "carrier" refers to a diluent, adjuvant, excipient, or vehicle with which the therapeutic is administered and includes, but is not limited to such liquids and powders that are hydrophilic substances, hydrophobic substances and substances that possess both hydrophilic and hydrophobic properties such as emulsifiers.

The term "therapeutically effective amount," as used herein, refers to the amount of active compound or pharmaceutical agent that elicits the biological or medicinal response in a tissue, system, or individual that is being sought by a researcher, healthcare provider or individual.

The term "w/w" as used herein, is intended to refer to mass fraction, i.e., the mass of a component divided by total mass of the whole. The term "% w/w" is intended to refer to the mass fraction multiplied by 100. Similarly, the term "w/v" refers to volume concentration, i.e., the mass of a component divided by total volume of the whole and the term "% w/v" refers to the volume concentration multiplied by 100.

The term "mouthfeel" as used herein is intended to refer to the physical sensations in the mouth produced by a particular food or drug.

The term API (active pharmaceutical ingredient) as used herein, refers to the component in a therapeutic medication or nutraceutical substance that is biologically active.

The term "unit dose" refers to a single drug delivery entity, e.g., a tablet, capsule, dry powder, solution, dispersion etc., that is administered to an individual. The amount administered may vary according to numerous factors, including, e.g., the age of the individual, the weight of the individual, the genetic makeup of the individual, and the severity of symptoms exhibited by the individual to whom the drug is administered.

The unit dosage form (powder, granulation, tablet, sphere, or capsule) may be packaged into a blister foil pack, a stick pack, a sachet, a pouch, a bottle, or any other self-contained unit. The unit dosage form may optionally be packaged as a dual package whereby the dry component (powder, granulation, tablet, sphere, capsule) may be combined with a solution component in an integrated package.

The term "excipient" as used herein is intended to mean components of a drug formulation other than the API that are added to a drug formulation to perform a specific function in the finished drug product. The excipient may aid in dissolution or dispersion of the API, beneficially alter the mouthfeel of the drug product, improve the taste profile of the drug product among other things. An excipient composition is intended to refer to a combination of a plurality of excipients that can be added to an API to produce a finished drug product.

The term NSAID (non-steroidal anti-inflammatory drug) as used herein, refers to drugs distinguished as a class from steroid compounds in which the drugs provide analgesic, antipyretic and anti-inflammatory effects. Prominent NSAIDs include aspirin, ibuprofen and naproxen although other NSAIDs include ketoprofen, sulindac, etodolac, fenoprofen, diclofenac, flurbiprofen, ketorolac, piroxicam, indomethacin, mefenamic, meloxicam, nabumetone, oxaprozin, ketoprofen, meclofenamate, tolmetin and salsalate.

Ibuprofen is an NSAID that is a non-specific cyclooxygenase inhibitor available over the counter and generally viewed as being relatively safe. (9, 10). Ibuprofen is sparingly soluble in water and different formulations have shown different absorption rates but equivalent bioavailability (11).

In various embodiments, ibuprofen may be present in certain formulations herein. In such formulations, the ibuprofen may be present in a quantity of from about 1.5% w/w, about 3.0% w/w, about 4.0% w/w, about 5.0% w/w or about 6.0% w/w up to about 9.0% w/w, about 10.0% w/w, about 11.0% w/w, about 12.0% w/w, about 13.0% w/w, about 14.0% w/w or about 15.0% w/w and, in particular, in an amount of about 1.5% w/w, about 3.0% w/w, about 4.0% w/w, about 5.0% w/w, about 6.0% w/w, about 7% w/w, about 7.5% w/w, about 8% w/w, about 9.0% w/w, about 10.0% w/w, about 11.0% w/w, about 12.0% w/w, about 13.0% w/w, about 14.0% w/w or about 15.0% w/w.

Formulations

In various embodiments, the present invention is directed to an excipient composition comprising a lecithin powder, a galactomannan, one or more sweetening agents, one or more flavoring agents and an organic acid in a preparation that when combined with an API produces a pharmaceutically acceptable preparation.

The invention utilizes functional excipients to produce a powder such that the following are achieved:

1. Acceptable properties of flow, density, compactability, suspendability, and dispersability are achieved for powder, solution, and suspension dosage forms.
2. Acceptable flavor profiles (intensity of flavor) and sufficient taste masking of one or more active pharmaceutical ingredients in the dosage forms listed in item 1 without the need for complex taste masking methods.
3. The same powder formulation can be processed utilizing but not limited to dry blending, roller compaction, wet granulation, spheronization and filled into foil/stick packs/sachets/pouches, compressed into chewable/swallowable/quick dissolving tablets and filled into capsules.
4. The invention allows for the powder dosage form to quickly dissolve in the mouth or the powder can be readily dissolved or suspended and dispersed using a small quantity of water and then taken by mouth.

In various embodiments, the formulation is a dispersion comprising ibuprofen, guar, lecithin, and flavors. In such a dispersion, isomalt, xylitol, citric acid, can be solubilized. In various other embodiments, the formulation can comprise components which are all solubilized.

Lecithin refers to a group of amphiphilic, surfactant compounds naturally occurring in plant and animal tissue and pharmaceutically useful as emulsifying agents. Lecithins can be found in fish, eggs, milk, soybeans, cotton seed, rapeseed and sunflower seeds. Chemically, the central structure of lecithin is a glycerol group with ester linkages to two long chain fatty acid groups and to an orthophosphate group. The orthophosphate group is then linked by an ester bond to a strongly basic choline group (12). The resultant molecule as shown below is a surfactant:

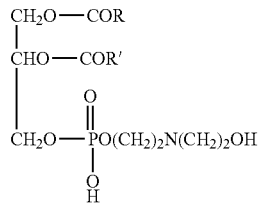

In processing from plant sources, the extract may be in oily liquid form as a result of the presence of liquid oily components which when further removed yields a granular or powder product.

Sunflower lecithin powder contains phosphatidyl choline, phosphatidyl inositol, phosphatidyl ethanolamine, and phosphatidic acid. In contrast to this, lecithin oil additionally contains oily components that result in the composition being in the form of an oily liquid.

The term "lecithin" or "lecithin powder" as used herein is intended to reference lecithin in powder or granular form and not lecithin oil.

The lecithin powder may be present in the excipient composition as well as in compositions containing an API and the excipient composition in an amount of from about 0.1% w/w, about 0.2% w/w, about 0.4% w/w up to about 0.6% w/w, about 0.7% w/w, about 0.8% w/w, about 0.9% w/w or about 1.0% w/w and, in particular, in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w or about 1.0% w/w.

The term "galactomannan" refers to a polysaccharide containing a mannose backbone and galactose side groups. Galactomannans may have a mannose to galactose ratio of from about 1:1 to about 4:1 and non-limiting examples include fenugreek gum, guar gum, tara gum and locust bean gum. Guar gum, in particular, may be useful as a component in the formulations herein.

The galactomannan, guar gum (mannose:galactose~2:1) may be present in the excipient composition as well as in compositions containing an API and the excipient composition in an amount of from about 0.05% w/w, about 0.1% w/w, about 0.2% w/w up to about 0.3% w/w, about 0.35% w/w, about 0.4% w/w, about 0.45% w/w or about 0.5% w/w and, in particular, in an amount of about 0.05% w/w, about 0.1% w/w, about 0.15% w/w, about 0.2% w/w, about 0.25% w/w, about 0.3% w/w, about 0.35% w/w, about 0.4% w/w, about 0.45 w/w or about 0.5% w/w.

Sweetening agents such as sugar alcohols, in particular, may be useful in the formulations herein. Sugar alcohols are polyols that may be derived from sugars in which either the aldehyde or the keto group may be reduced. These may include (with chain length indicated in parentheses): glycerol (3-carbon), erythritol (4-carbon), threitol (4-carbon), arabitol (5-carbon), xylitol (5-carbon), ribitol (5-carbon), mannitol (6-carbon), sorbitol, (6-carbon), galactitol (6-carbon), fucitol (6-carbon), iditol (6-carbon), inositol (6-carbon cyclic sugar alcohol), volemitol (7-carbon), isomalt (12-carbon), maltitol (12-carbon), lactitol (12-carbon), maltotriitol (18-carbon) and maltotetraitol (24-carbon). Xylitol and isomalt, in particular, may be useful in the formulations herein. Xylitol may be present in the excipient composition as well as in compositions containing an API and the excipient composition in an amount of from about 1% w/w, about 5% w/w, about 10% w/w or about 15% w/w up to about 25% w/w, about 30% w/w, about 35% w/w or about 40% w/w and, in particular, in an amount of about 5% w/w, about 10% w/w, about 15% w/w, about 20% w/w, about 25% w/w, about 30% w/w, about 35% about 40% w/w.

Isomalt may be present in the excipient composition as well as in compositions containing an API and the excipient composition in an amount of from about 10% w/w, 15% w/w, 20% w/w, 25% w/w, 30% w/w, 35% w/w, 40% w/w, about 45% w/w, about 50% w/w, about 55% w/w, about 60% w/w or about 65% w/w up to about 75% w/w, about 80% w/w or about 85% w/w and, in particular, in an amount of about 40% w/w, about 45% w/w, about 50% w/w, about 55% w/w, about 60% w/w, about 65% w/w, about 70% w/w, about 75% w/w, about 80% w/w, about 85% w/w, or about 90% w/w. Other fillers or diluents can include dextrins, maltodextrins, fructose, and the like in the same amounts. Those of skill in the art will recognize other fillers and diluents suitable in the present formulation.

Flavoring agents may also be included in the formulations herein. Flavoring agents are additives that modify or enhance the taste and the aroma of orally consumed substances. Examples of the flavoring agent that may be used in the formulations herein include fruity flavoring agents such as cherry, strawberry and raspberry as well as other flavoring agents such as peppermint, spearmint, lemon, etc. Cherry, strawberry and raspberry flavorings, in particular, may be useful in the formulations herein.

The cherry, strawberry and raspberry flavoring, may be present in the excipient composition as well as in compositions containing an API and the excipient composition in an amount of from about 0.02% w/w, about 0.04% w/w, about 0.08% w/w, about 0.1% w/w, about 0.2% w/w, about 0.4% w/w, about 0.8% w/w up to about 1.2% w/w, about 1.4% w/w, about 1.6% w/w, about 1.8% w/w or about 2.0% w/w and, in particular, in an amount of about 0.02% w/w, about 0.04% w/w, about 0.08% w/w, about 0.1% w/w, about 0.2% w/w, about 0.4% w/w, about 0.6% w/w, about 0.8% w/w, about 1.0% w/w, about 1.2% w/w, about 1.4% w/w, about 1.6% w/w, about 1.8% w/w, about 2.0% w/w, or about 3% w/w.

The formulations herein may also include an organic acid such as citric acid, tartaric acid, ascorbic acid, fumaric acid, malic acid, adipic acid, succinic acid etc. Citric acid, in particular, may be useful in the formulations herein.

Citric acid may be present in the excipient composition as well as in compositions containing an API and the excipient composition in an amount of from about 0.025% w/w, about 0.05% w/w, about 0.1% w/w up to about 0.15% w/w, about 0.175% w/w, about 0.2% w/w, about 0.225 w/w or about 0.25 w/w and, in particular, in an amount of about 0.025 w/w, about 0.05% w/w, about 0.0755% w/w, about 0.1% w/w, about 0.125% w/w, about 0.15 w/w, about 0.175 w/w, about 0.2% w/w, about 0.225 w/w or about 0.25% w/w. Other acidulants may be included in the present formulation in the same amounts, such as malic acid, formic acid, and the like. Those of skill in the art will recognize other acidulants useful in the present formulation.

The formulations herein may be processed by dry blending, roller compaction, wet granulation, spheronization and filled into foil/stick packs/sachets/pouches, compressed into chewable/swallowable/quick dissolving tablets and filled into capsules.

EXAMPLES

Aspects of the present teachings may be further understood in light of the following examples, which should not be construed as limiting the scope of the present teachings in any way. Unless otherwise indicated, the amount of formulation tested was 1.33 g or 2.66 g, which will be identified in the context of the examples below.

Example 1

This example evaluated a prototype formula with Isomalt to ascertain preliminary information on mouth feel, flavor intensity, and sweetness.

TABLE 1a

| Blend Fill Weight (mg) | API (mg) | Batch (units) | Batch Weight (g) |
|---|---|---|---|
| 500.0 | 100.0 | 100 | 50 |

TABLE 1B

| Ingredient | Vendor | Lot Number | % Concentration | mg/blend fill | g/batch size | kg/batch size |
|---|---|---|---|---|---|---|
| Ibuprofen, USP | SI Group | 7050-3921 | 20.000 | 100.000 | 10.000 | 0.010 |
| Isomalt (Galen IQ) | Beneo GMBH | L1216907U2 | 79.800 | 399.000 | 39.900 | 0.040 |
| Natural Cherry Flavor CX91 #32839 | Virginia Dare | S79317 | 0.100 | 0.500 | 0.050 | 0.000 |
| Edicol 60-70 (guar gum) | Lucid | 152/2016 | 0.100 | 0.500 | 0.050 | 0.000 |
| TOTAL | | | 100.000 | 500.000 | 50.000 | 0.050 |

The blend process was as follows.

1. Screen Ibuprofen and Isomalt through a #20 screen.
2. Screen flavor through a #40 screen.
3. Add the following into a plastic bag in the following order:
   a. ½ Isomalt
   b. Ibuprofen
   c. flavor
   d. Guar gum
   e. ½ Isomalt
4. Blend by rotating the bag at a consistent pace for 3 minutes.

Results:

There was no bitter taste in mouth with a little to moderate burn in the throat. Flavor intensity was not enough.

Example 2

This example evaluated a formula with Xylitol to lessen throat burning, increase flavor, and increase sweetness.

TABLE 2a

| Blend Fill Weight (mg) | API (mg) | Batch (units) | Batch Weight (g) |
|---|---|---|---|
| 500.0 | 100.0 | 100 | 50 |

TABLE 2B

| Ingredient | Vendor | Lot Number | % Concentration | mg/blend fill | g/batch size | kg/batch size |
|---|---|---|---|---|---|---|
| Ibuprofen, USP | SI Group | 7050-3921 | 20.000 | 100.000 | 10.000 | 0.010 |
| Xylitol (Xivia CM170) | Dupont | 1942791649 | 78.900 | 394.500 | 39.450 | 0.039 |
| Natural Cherry Flavor CX91 #32839 | Virginia Dare | S79317 | 1.000 | 5.000 | 0.500 | 0.001 |
| Edicol 60-70 (guar gum) | Lucid | 152/2016 | 0.100 | 0.500 | 0.050 | 0.000 |
| TOTAL | | | 100.000 | 500.000 | 50.000 | 0.050 |

The blend process was as follows.
1. Screen Ibuprofen and Xylitol through a #20 screen.
2. Screen flavor through a #40 screen.
3. Add the following into a plastic bag in the following order:
   a. ½ Xylitol
   b. Ibuprofen
   c. flavor
   d. Guar gum
   e. ½ Xylitol
4. Blend by rotating the bag at a consistent pace for 3 minutes.

Results:
There was some bitterness in mouth and some burning. Flavor intensity needs to be improved. Sweetness level seemed acceptable. Body may be improved by increasing gum level.

Example 3

This example evaluated a formulation with Xylitol to lessen throat burning and with increased flavor and sweetness components.

TABLE 3a

| Blend Fill Weight (mg) | API (mg) | Batch (units) | Batch Weight (g) |
|---|---|---|---|
| 1,000.0 | 100.0 | 50 | 50 |

TABLE 3B

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 43.875 | 438.750 | 21.938 | 0.022 |
| Xylitol (Xivia CM170) | Dupont | 1942791649 | 43.875 | 438.750 | 21.938 | 0.022 |
| All Natural Cherry Flavor CX91 #32839 | Virginia Dare | S79317 | 2.000 | 20.000 | 1.000 | 0.001 |
| Edicol 60-70 (guar gum) | Lucid | 152/2016 | 0.250 | 2.500 | 0.125 | 0.000 |
| TOTAL | | | 100.000 | 1000.000 | 50.000 | 0.050 |

The blend process was as follows.

1. Screen Ibuprofen, Isomalt, and Xylitol through a #20 screen.
2. Screen flavor through a #40 screen.
3. Add the following into a plastic bag in the following order:
   a. Isomalt
   b. Ibuprofen
   c. flavor
   d. Guar gum
   e. Xylitol
4. Blend by rotating the bag at a consistent pace for 3 minutes.

Results:

There was very little burning after formulation was completely wetted in the mouth. Sweetness was acceptable. Flavor needs to be more intense. Mouthfeel was acceptable.

When taken wet with 5 g of filtered water, flavor and sweetness was comparable to dry intake with very low level of burning.

This Formula went into solution easily except that the ibuprofen seemed to agglomerate and form a film at the top. The formulation needs a natural surfactant so that the ibuprofen will disperse uniformly into the water.

Example 4

This example evaluated a formulation with a 3:1 ratio of Isomalt to Xylitol and with increased flavor concentration.

TABLE 4a

| Blend Fill Weight (mg) | API (mg) | Batch (units) | Batch Weight (g) |
|---|---|---|---|
| 1,000.0 | 100.0 | 50 | 50 |

TABLE 4b

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 64.313 | 643.130 | 32.157 | 0.032 |
| Xylitol (Xivia CM170) | Dupont | 1942791649 | 21.437 | 214.370 | 10.719 | 0.011 |
| All Natural Cherry Flavor CX91 #32839 | Virginia Dare | S79317 | 4.000 | 40.000 | 2.000 | 0.002 |
| Edicol 60-70 (guar gum) | Lucid | 152/2016 | 0.250 | 2.500 | 0.125 | 0.000 |
| | TOTAL | | 100.000 | 1000.000 | 50.000 | 0.050 |

The blend process was as follows.
1. Screen Ibuprofen, Isomalt, and Xylitol through a #20 screen.
2. Screen flavor through a #40 screen.
3. Add the following into a plastic bag in the following order:
   a. Isomalt
   b. Ibuprofen
   c. flavor
   d. Guar gum
   e. Xylitol
4. Blend by rotating the bag at a consistent pace for 3 minutes.

Results:

Sweetness was acceptable, however it might be desirable to add more sweetener. There was no bitter taste and virtually no burning. Flavor intensity was improved. Mouthfeel was acceptable.

Example 5

This example evaluated the replacement of Virginia Dare (VD) Cherry with Gold Coast (GC) Organic Cherry at the same concentration.

TABLE 5a

| Blend Fill Weight (mg) | API (mg) | Batch (units) | Batch Weight (g) |
|---|---|---|---|
| 1,000.0 | 100.0 | 50 | 50 |

TABLE 5b

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 64.313 | 643.130 | 32.157 | 0.032 |
| Xylitol (Xivia CM170) | Dupont | 1942791649 | 21.437 | 214.370 | 10.719 | 0.011 |
| Organic Cherry Flavor #650818 | Gold Coast | Dec. 2, 2016 | 4.000 | 40.000 | 2.000 | 0.002 |
| Edicol 60-70 (guar gum) | Lucid | 152/2016 | 0.250 | 2.500 | 0.125 | 0.000 |
| | TOTAL | | 100.000 | 1000.000 | 50.000 | 0.050 |

The blend process was as follows.
1. Screen Ibuprofen, Isomalt, and Xylitol through a #20 screen.
2. Screen flavor through a #40 screen.
3. Add the following into a plastic bag in the following order:
   a. Isomalt
   b. Ibuprofen
   c. flavor
   d. Guar gum
   e. Xylitol
4. Blend by rotating the bag at a consistent pace for 3 minutes.

Results:

There was no bitter taste or burning. Cherry flavor is a juicy bright flavor that is very good. Mouthfeel was acceptable and sufficiently sweet.

When taken wet with 5 ml of water, a significant portion of undissolved powder filmed and agglomerated on top of the water surface. Sweetness and flavor intensity was similar to that when taken dry and burning was too apparent.

Example 6

This example compares Strawberry and Raspberry Flavors from VD and GC at the same concentration as Cherry flavoring.

TABLE 6a

| Blend Fill Weight (mg) | API (mg) | Batch (units) | Batch Weight (g) |
|---|---|---|---|
| 1,000.0 | 100.0 | 50 | 50 |

TABLE 6b

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 64.313 | 643.130 | 32.157 | 0.032 |
| Xylitol (Xivia CM170) | Dupont | 1942791649 | 21.437 | 214.370 | 10.719 | 0.011 |
| IBU-006-1 All Natural Strawberry Flavor #34775 | Virginia Dare | S79315 | 4.000 | 40.000 | 2.000 | 0.002 |
| IBU-006-2 All Natural Raspberry Flavor #26507 | Virginia Dare | S79313 | | | | |
| IBU-006-3 Organic Strawberry Flavor #311904 | Gold Coast | Dec. 2, 2016 | | | | |
| IBU-006-4 Organic Raspberry Flavor #325361 | Gold Coast | Dec. 2, 2016 | | | | |
| Edicol 60-70 (guar gum) | Lucid | 152/2016 | 0.250 | 2.500 | 0.125 | 0.000 |
| | TOTAL | | 100.000 | 1000.000 | 50.000 | 0.050 |

The blend process was as follows.
1. Screen Ibuprofen, Isomalt, and Xylitol through a #20 screen.
2. Screen flavor through a #40 screen.
3. Add the following into a plastic bag in the following order:
  a. Isomalt
  b. Ibuprofen
  c. flavor
  d. Guar gum
  e. Xylitol
4. Blend by rotating the bag at a consistent pace for 3 minutes.

Results:
IBU-006-1: Taste was pleasant and not bitter and with very little burning after rinsing mouth with water.

IBU-006-2: Flavor did not taste mask as well as formulation IBU-006-1. Bitterness and burning were apparent. The powder blend had a pink color due to flavoring.

IBU-006-3: Flavor was very pleasant with no bitterness or burning.

IBU-006-4: Flavor was Intense with no bitterness or burning.

Example 7

This example compared VD Cherry-Strawberry to GC Cherry-Strawberry combinations at the same ratio and total concentrations.

TABLE 7a

| Blend Fill Weight (mg) | API (mg) | Batch (units) | Batch Weight (g) |
|---|---|---|---|
| 1,000.0 | 100.0 | 50 | 50 |

TABLE 7b

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 64.313 | 643.130 | 32.157 | 0.032 |
| Xylitol (Xivia CM170) IBU-007-1 | Dupont | 1942791649 | 21.437 | 214.370 | 10.719 | 0.011 |
| All Natural Cherry Flavor CX91 #32839 | Virginia Dare | S79317 | 2.000 | 20.000 | 1.000 | 0.001 |
| All Natural Strawberry Flavor #34775 IBU-007-1 | Virginia Dare | S79315 | 2.000 | 20.000 | 1.000 | 0.001 |
| Organic Cherry Flavor #650818 | Gold Coast | Dec. 2, 2016 | 2.000 | 20.000 | 1.000 | 0.001 |
| Organic Strawberry Flavor #311904 | Gold Coast | Dec. 2, 2016 | 2.000 | 20.000 | 1.000 | 0.001 |
| Edicol 60-70 (guar gum) | Lucid | 152/2016 | 0.250 | 2.500 | 0.125 | 0.000 |
| TOTAL | | | 100.000 | 1000.000 | 50.000 | 0.050 |

The blend process was as follows.
1. Screen Ibuprofen, Isomalt, and Xylitol through a #20 screen.
2. Screen flavor through a #40 screen.
3. Add the following into a plastic bag in the following order:
   a. Isomalt
   b. Ibuprofen
   c. flavor
   d. Guar gum
   e. Xylitol
4. Blend by rotating the bag at a consistent pace for 3 minutes Results:

IBU-007-1: With 1 g sample, flavor combination was pleasant with no bitterness and minor burning after completely wetted in the mouth. Strawberry flavor was dominant.

IBU-007-2: With 1 g sample, flavor combination was very good with no burning or bitterness after completely wetted in the mouth. Strawberry flavor was dominant. With larger amount of 2 g, the cherry and strawberry flavors could be detected with no bitterness or burning after complete wetted in the mouth by swishing the suspension around in the mouth.

Example 8

This example compared VD Cherry-Strawberry-Raspberry flavorings to GC Cherry-Strawberry-Raspberry flavorings.

TABLE 8a

| Blend Fill Weight (mg) | API (mg) | Batch (units) | Batch Weight (g) |
|---|---|---|---|
| 1,000.0 | 100.0 | 50 | 50 |

TABLE 8b

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 64.313 | 643.130 | 32.157 | 0.032 |
| Xylitol (Xivia CM170) | Dupont | 1942791649 | 21.437 | 214.370 | 10.719 | 0.011 |
| IBU-008-1 | | | | | | |
| All Natural Cherry Flavor CX91 #32839 | Virginia Dare | S79317 | 1.340 | 13.400 | 0.670 | 0.001 |
| All Natural Strawberry Flavor #34775 | Virginia Dare | S79315 | 1.330 | 13.300 | 0.665 | 0.001 |
| All Natural Raspberry Flavor #26507 | Virginia Dare | S79313 | 1.330 | 13.300 | 0.665 | 0.001 |
| IBU-008-2 | | | | | | |
| Organic Cherry Flavor #650818 | Gold Coast | Dec. 2, 2016 | 1.340 | 13.400 | 0.670 | 0.001 |
| Organic Strawberry Flavor #311904 | Gold Coast | Dec. 2, 2016 | 1.330 | 13.300 | 0.665 | 0.001 |
| Organic Raspberry Flavor #325361 | Gold Coast | Dec. 2, 2016 | 1.330 | 13.300 | 0.665 | 0.001 |
| Edicol 60-70 (guar gum) | Lucid | 152/2016 | 0.250 | 2.500 | 0.125 | 0.000 |
| | | TOTAL | 100.000 | 1000.000 | 50.000 | 0.050 |

The blend process was as follows.
1. Screen Ibuprofen, Isomalt, and Xylitol through a #20 screen.
2. Screen flavor through a #40 screen.
3. Add the following into a plastic bag in the following order:
   a. Isomalt
   b. Ibuprofen
   c. flavor
   d. Guar gum
   e. Xylitol
4. Blend by rotating the bag at a consistent pace for 3 minutes.

Results:

IBU-008-1: With 2 g sample, flavor was very pleasant with good balance, spicy after notes, no bitterness and little burning in throat.

IBU-008-2: With 2 g sample, flavor was very pleasant with strawberry dominance, no bitterness and some irritation in throat.

Example 9

This example evaluated Sunflower Lecithin to aid in dispersion of Ibuprofen in suspension form. Also evaluated were a reduced amount of strawberry flavoring.

TABLE 9a

| Blend Fill Weight (mg) | API (mg) | Batch (units) | Batch Weight (g) |
|---|---|---|---|
| 1,000.0 | 100.0 | 50 | 50 |

TABLE 9a

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 64.373 | 643.730 | 32.187 | 0.032 |
| Xylitol (Xivia CM170) | Dupont | 1942791649 | 21.457 | 214.570 | 10.729 | 0.011 |
| IBU-009-1 All Natural Cherry Flavor CX91 #32839 | Virginia Dare | S79317 | 1.340 | 13.400 | 0.670 | 0.001 |
| All Natural Strawberry Flavor #34775 | Virginia Dare | S79315 | 1.000 | 10.000 | 0.500 | 0.001 |
| All Natural Raspberry Flavor #26507 | Virginia Dare | S79313 | 1.330 | 13.300 | 0.665 | 0.001 |
| IBU-009-2 Organic Cherry Flavor #652865 | Gold Coast | Dec. 2, 2016 | 1.340 | 13.400 | 0.670 | 0.001 |
| Organic Strawberry Flavor #400938 | Gold Coast | Dec. 2, 2016 | 1.000 | 10.000 | 0.500 | 0.001 |
| Organic Raspberry Flavor #325361 | Gold Coast | Dec. 2, 2016 | 1.330 | 13.300 | 0.665 | 0.001 |
| Edicol 60-70 (guar gum) | Lucid | 152/2016 | 0.250 | 2.500 | 0.125 | 0.000 |
| Sunflower Lecithin | Now | None on container | 0.250 | 2.500 | 0.125 | 0.000 |
| TOTAL | | | 100.000 | 1000.000 | 50.000 | 0.050 |

The blend process was as follows.
1. Screen Ibuprofen, Isomalt, and Xylitol through a #20 screen.
2. Screen flavor and lecithin through a #40 screen.
3. Add the following into a plastic cup in the following order:
   a. Isomalt
   b. Ibuprofen
   c. Lecithin
   d. flavor
   e. Guar gum
   f. Xylitol
4. Blend by rotating the plastic cup at a consistent pace for 3 minutes.

Results:
IBU-009-2: With 2 g dry sample, there was good flavor balance with very little drug bitterness or burning.

With 2 g sample in 1 tsp. water, flavor was good with no drug bitterness or burning. Suspension was white, cloudy and uniform.

With 2 g in 2 tsp. water flavor was lighter with adequate sweetness. Suspension was white cloudy, and uniform.

Example 10

This example evaluated a formulation containing GC Cherry with VD Strawberry and Raspberry.

TABLE 10a

| Blend Fill Weight (mg) | API (mg) | Batch (units) | Batch Weight (g) |
|---|---|---|---|
| 1,000.0 | 100.0 | 50 | 50 |

TABLE 10b

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 64.126 | 641.260 | 32.063 | 0.032 |
| Xylitol (Xivia CM170) | Dupont | 1942791649 | 21.374 | 213.740 | 10.687 | 0.011 |

TABLE 10b-continued

| Ingredient | Vendor | Lot Number | % Concentration | mg/blend fill | g/batch size | kg/batch size |
|---|---|---|---|---|---|---|
| Organic Cherry Flavor #652865 | Gold Coast | 12/2/2016 | 1.500 | 15.000 | 0.750 | 0.001 |
| All Natural Strawberry Flavor #34775 | Virginia Dare | S79315 | 1.000 | 10.000 | 0.500 | 0.001 |
| All Natural Raspberry Flavor #26507 | Virginia Dare | S79313 | 1.500 | 15.000 | 0.750 | 0.001 |
| Edicol 60-70 (guar gum) | Lucid | 152/2016 | 0.250 | 2.500 | 0.125 | 0.000 |
| Sunflower Lecithin | Now | None on container | 0.250 | 2.500 | 0.125 | 0.000 |
| | TOTAL | | 100.000 | 1000.000 | 50.000 | 0.050 |

The blend process was as follows.
1. Screen Ibuprofen, Isomalt, and Xylitol through a #20 screen.
2. Screen flavor through a #40 and lecithin through a #100 screen.
3. Add the following into a plastic cup in the following order:
  a. Isomalt
  b. Ibuprofen
  c. Lecithin
  d. flavor
  e. Guar gum
  f. Xylitol
4. Blend by rotating the plastic cup at a consistent pace for 3 minutes.

Results:
With 2 g dry sample, there was excellent balance of flavor with no bitterness and very low irritation and burning.

With 2 g in 1 tsp. water, the suspension was light pink color and cloudy with a few dark specs coming from raspberry. These dissolved with a little more shaking. Flavor was good with little throat irritation.

With 2 g dry sample swallowed, flavor was excellent with no bitterness and low to moderate throat irritation which went away in a few minutes.

Example 11

This example evaluated a blend with 5% Ibuprofen to reduce or eliminate throat irritation.

TABLE 11a

| Blend Fill Weight (mg) | API (mg) | Batch (units) | Batch Weight (g) |
|---|---|---|---|
| 2,000.0 | 100.0 | 25 | 50 |

TABLE 11b

| Ingredient | Vendor | Lot Number | % Concentration | mg/blend fill | g/batch size | kg/batch size |
|---|---|---|---|---|---|---|
| Ibuprofen, USP | SI group | 7050-3921 | 5.000 | 100.000 | 2.500 | 0.003 |
| Isomalt (Galen IQ) | Beneo GMBH | L1216907U2 | 67.876 | 1357.520 | 33.938 | 0.034 |
| Xylitol (Xivia CM170) | Dupont | 1942791649 | 22.624 | 452.480 | 11.312 | 0.011 |
| Organic Cherry Flavor #652865 | Gold Coast | Dec. 2, 2016 | 1.500 | 30.000 | 0.750 | 0.001 |
| All Natural Strawberry Flavor #34775 | Virginia Dare | S79315 | 1.000 | 20.000 | 0.500 | 0.001 |
| All Natural Raspberry Flavor #26507 | Virginia Dare | S79313 | 1.500 | 30.000 | 0.750 | 0.001 |
| Edicol 60-70 (guar gum) | Lucid | 152/2016 | 0.250 | 5.000 | 0.125 | 0.000 |
| Sunflower Lecithin | Now | None on container | 0.250 | 5.000 | 0.125 | 0.000 |
| | TOTAL | | 100.000 | 2000.000 | 50.000 | 0.050 |

The blend process was as follows.

1. Screen Ibuprofen, Isomalt, and Xylitol through a #20 screen.
2. Screen flavor through a #40 and lecithin through a #100 screen. (lecithin was difficult to screen through #100).
3. Add the following into a plastic cup in the following order:
   a. Isomalt
   b. Ibuprofen
   c. Lecithin
   d. flavor
   e. Guar gum
   f. Xylitol
4. Blend by rotating the plastic cup at a consistent pace for 3 minutes.

Results:

With 4 g dry sample taste was excellent with no bitterness and virtually no throat irritation. The amount of powder in the mouth was too much.

With 4 g sample in 1 tsp. water, swallowed, the suspension was light pink and cloudy with excellent dispersion and good flavor, good mouthfeel, no bitterness and virtually no irritation.

Example 12

This example evaluated a blend with peppermint at 0.25% to reduce or eliminate throat irritation.

TABLE 12a

| Blend Fill Weight (mg) | API (mg) | Batch (units) | Batch Weight (g) |
|---|---|---|---|
| 1,000.0 | 100.0 | 50 | 50 |

TABLE 12b

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 63.938 | 639.380 | 31.969 | 0.032 |
| Xylitol (Xivia CM170) | Dupont | 1942791649 | 21.312 | 213.120 | 10.656 | 0.011 |
| Organic Cherry Flavor #652865 | Gold Coast | Dec. 2, 2016 | 1.500 | 15.000 | 0.750 | 0.001 |
| All Natural Strawberry Flavor #34775 | Virginia Dare | S79315 | 1.000 | 10.000 | 0.500 | 0.001 |
| All Natural Raspberry Flavor #26507 | Virginia Dare | S79313 | 1.500 | 15.000 | 0.750 | 0.001 |
| Organic Peppermint Flavor #315160 | Gold Coast | Dec. 2, 2016 | 0.250 | 2.500 | 0.125 | 0.000 |
| Edicol 60-70 (guar gum) | Lucid | 152/2016 | 0.250 | 2.500 | 0.125 | 0.000 |
| Sunflower Lecithin | Now | None on container | 0.250 | 2.500 | 0.125 | 0.000 |
| TOTAL | | | 100.000 | 1000.000 | 50.000 | 0.050 |

The blend process was as follows.
1. Screen Ibuprofen, Isomalt, and Xylitol through a #20 screen.
2. Screen flavor through a #40 and lecithin through a #40 screen.
3. Add the following into a plastic cup in the following order:
 a. Isomalt
 b. Ibuprofen
 c. Lecithin
 d. flavor
 e. Guar gum
 f. Xylitol
4. Blend by rotating the plastic cup at a consistent pace for 3 minutes.

Results:

With 2 g dry sample swallowed, there was not enough peppermint which could hardly be detectable and no bitterness, but too much throat burn.

Example 13

This example evaluated a blend with Peppermint at 1% to reduce or eliminate throat irritation.

TABLE 13a

| Blend Fill Weight (mg) | API (mg) | Batch (units) | Batch Weight (g) |
|---|---|---|---|
| 1,000.0 | 100.0 | 50 | 50 |

TABLE 13b

| Ingredient | Vendor | Lot Number | % Concentration | mg/blend fill | g/batch size | kg/batch size |
|---|---|---|---|---|---|---|
| Ibuprofen, USP | SI group | 7050-3921 | 10.000 | 100.000 | 5.000 | 0.005 |
| Isomalt (Galen IQ) | Beneo GMBH | L1216907U2 | 63.375 | 633.750 | 31.688 | 0.032 |
| Xylitol (Xivia CM170) | Dupont | 1942791649 | 21.125 | 211.250 | 10.563 | 0.011 |
| Organic Cherry Flavor #652865 | Gold Coast | Dec. 2, 2016 | 1.500 | 15.000 | 0.750 | 0.001 |
| All Natural Strawberry Flavor #34775 | Virginia Dare | S79315 | 1.000 | 10.000 | 0.500 | 0.001 |
| All Natural Raspberry Flavor #26507 | Virginia Dare | S79313 | 1.500 | 15.000 | 0.750 | 0.001 |
| Organic Peppermint Flavor #315160 | Gold Coast | Dec. 2, 2016 | 1.000 | 10.000 | 0.500 | 0.001 |
| Edicol 60-70 (guar gum) | Lucid | 152/2016 | 0.250 | 2.500 | 0.125 | 0.000 |
| Sunflower Lecithin | Now | None on container | 0.250 | 2.500 | 0.125 | 0.000 |
| TOTAL | | | 100.000 | 1000.000 | 50.000 | 0.050 |

The blend process was as follows.
1. Screen Ibuprofen, Isomalt, and Xylitol through a #20 screen.
2. Screen flavor through a #40 and lecithin through a #40 screen.
3. Add the following into a plastic cup in the following order:
   a. Isomalt
   b. Ibuprofen
   c. Lecithin
   d. flavor
   e. Guar gum
   f. Xylitol
4. Blend by rotating the plastic cup at a consistent pace for 3 minutes.

Results:

With 2 g dry sample swallowed, the cool mint and fruit flavor of the combination was excellent with no bitterness and little throat irritation.

Example 14

This example evaluated a blend with 7.5% concentration of Ibuprofen to reduce or eliminate throat irritation.

TABLE 14a

| Blend Fill Weight (mg) | API (mg) | Batch (units) | Batch Weight (g) |
|---|---|---|---|
| 1,333.3 | 100.0 | 38.0 | 50.667 |

TABLE 14b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 66.000 | 880.000 | 33.440 | 0.033 |
| Xylitol (Xivia CM170) | Dupont | 1942791649 | 22.000 | 293.333 | 11.147 | 0.011 |
| Organic Cherry Flavor #652865 | Gold Coast | Dec. 2, 2016 | 1.500 | 20.000 | 0.760 | 0.001 |
| All Natural Strawberry Flavor #34775 | Virginia Dare | S79315 | 1.000 | 13.333 | 0.507 | 0.001 |
| All Natural Raspberry Flavor #26507 | Virginia Dare | S79313 | 1.500 | 20.000 | 0.760 | 0.001 |
| Edicol 60-70 (guar gum) | Lucid | 152/2016 | 0.250 | 3.333 | 0.127 | 0.000 |
| Sunflower Lecithin | Now | None on container | 0.250 | 3.333 | 0.127 | 0.000 |
| TOTAL | | | 100.000 | 1333.333 | 50.667 | 0.051 |

The blend process was as follows.
1. Screen Ibuprofen, Isomalt, and Xylitol through a #20 screen.
2. Screen flavor through a #40 and lecithin through a #40 screen.
3. Add the following into a plastic cup in the following order:
  a. Isomalt
  b. Ibuprofen
  c. Lecithin
  d. flavor
  e. Guar gum
  f. Xylitol
4. Blend by rotating the plastic cup at a consistent pace for 3 minutes.
Results:
With 2.666 g dry sample, swallowed, flavor was excellent with no bitterness and very little throat burning.
With 2.666 g sample in 1 tsp. water, flavor was excellent with no bitterness and no throat burning.

Example 15

This example evaluated an agglomeration blending approach for Ibuprofen and Lecithin with 50:50 ratio of Ibuprofen to Lecithin.
Ibuprofen/Lecithin Agglomeration/Coating/Granulation formulation.

TABLE 15a

| % Solids in $H_2O$ | Batch Weight (g) | Total Coating (g) | % Lecithin in $H_2O$ | Total $H_2O$ (g) |
| --- | --- | --- | --- | --- |
| 82.9 | 11.000 | 13.269 | 70.8 | 2.269 |

TABLE 15b

| Ingredient | Vendor | Lot Number | % in Granulation | g/batch size | kg/batch size |
| --- | --- | --- | --- | --- | --- |
| Ibuprofen, USP | SI group | 7050-3921 | 50.000 | 5.500 | 0.006 |
| Sunflower Lecithin | Now | None on container | 50.000 | 5.500 | 0.006 |
| TOTAL | | | 100.000 | 11.000 | 0.011 |

The following process was used.
1. Screen lecithin through #40 screen.
2. Screen Ibuprofen through #20 screen.
3. Blend lecithin and ibuprofen for 3 minutes.
4. Weigh water in Suitable container. Add incrementally with stirring until an agglomeration is achieved.
5. Dry at room temperature until thoroughly dry.
6. Screen granulation through a #20 screen.
Results:
The agglomeration was too elastic too screen into powder.

Example 16

This example evaluated an agglomeration blending approach for ibuprofen and lecithin with 90:10 ratio of ibuprofen to lecithin.
Ibuprofen/Lecithin Agglomeration/Coating/Granulation formulation.

TABLE 16a

| % Solids in $H_2O$ | Batch Weight (g) | Total Coating (g) | % Lecithin in $H_2O$ | Total $H_2O$ (g) |
| --- | --- | --- | --- | --- |
| 82.7 | 6.112 | 7.391 | 32.3 | 1.279 |

TABLE 16b

| Ingredient | Vendor | Lot Number | % in Granulation | g/batch size | kg/batch size |
| --- | --- | --- | --- | --- | --- |
| Ibuprofen, USP | SI group | 7050-3921 | 90.000 | 5.501 | 0.006 |
| Sunflower Lecithin | Now | None on container | 10.000 | 0.611 | 0.001 |
| TOTAL | | | 100.000 | 6.112 | 0.006 |

The following process was used.
1. Screen lecithin through #40 screen.
2. Screen Ibuprofen through #20 screen.
3. Blend lecithin and ibuprofen for 3 minutes.
4. Weigh water in Suitable container. Add incrementally with stirring until an agglomeration is achieved.
5. Dry at room temperature until thoroughly dry.
6. Screen granulation through a #20 screen.
Powder Fill Formulation TABLE 16c

| Blend Fill Weight (mg) | API (mg) | Batch (units) | Batch Weight (g) |
| --- | --- | --- | --- |
| 1,000.0 | 100.0 | 45 | 45 |

TABLE 16d

| Ingredient | Vendor | Lot Number | % Granulation in Blend | % in Blend | mg in blend | g/batch size | kg/batch size |
| --- | --- | --- | --- | --- | --- | --- | --- |
| Agglomeration-Coating-Granulation | | | | | | | |
| Ibuprofen, USP | SI group | 7050-3921 | 11.111 | 10.000 | 100.000 | 4.500 | 0.005 |
| Sunflower Lecithin | Now | None on container | | 1.111 | 11.111 | 0.500 | 0.001 |
| TOTAL | | | | | 111.111 | 5.000 | 0.005 |
| Powder Blend | | | | | | | |
| Isomalt (Galen IQ) | Beneo GMBH | L1216907U2 | — | 63.480 | 634.800 | 28.566 | 0.029 |

TABLE 16d-continued

| Ingredient | Vendor | Lot Number | % Granulation in Blend | % in Blend | mg in blend | g/batch size | kg/batch size |
|---|---|---|---|---|---|---|---|
| Xylitol (Xivia CM170) | Dupont | 1942791649 | — | 21.159 | 211.590 | 9.522 | 0.010 |
| Organic Cherry Flavor #652865 | Gold Coast | Dec. 2, 2016 | — | 1.500 | 15.000 | 0.675 | 0.001 |
| All Natural Strawberry Flavor #34775 | Virginia Dare | S79315 | — | 1.000 | 10.000 | 0.450 | 0.000 |
| All Natural Raspberry Flavor #26507 | Virginia Dare | S79313 | — | 1.500 | 15.000 | 0.675 | 0.001 |
| Edicol 60-70 (guar gum) | Lucid | 152/2016 | — | 0.250 | 2.500 | 0.113 | 0.000 |
| | | TOTAL | | 100.000 | 1000.001 | 45.000 | 0.045 |

The blend Process was as follows.
1. Screen Isomalt and Xylitol through a #20 screen.
2. Screen flavors through a #40 screen.
3. Add the following into a plastic cup in the following order:
   a. Isomalt
   b. Ibuprofen-lecithin granulation
   d. flavor
   e. Guar gum
   f. Xylitol
4. Blend by rotating the plastic cup at a consistent pace for 3 minutes.

Results:
Blend did not appear uniform. It was screened through a #40 mesh and re-blended for 3 minutes.

With 2 g dry sample, swallowed, there was no bitter, but there was considerable burning on tongue. There was no throat irritation.

Example 17

This example evaluated a blend of 7.5% Ibuprofen with Lecithin at 0.5%.

TABLE 17a

| Blend Fill Weight (mg) | API (mg) | Batch (units) | Batch Weight (g) |
|---|---|---|---|
| 1,333.3 | 100.0 | 38.0 | 50.665 |

TABLE 17b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 67.550 | 900.644 | 34.224 | 0.034 |
| Xylitol (Xivia CM170) | Dupont | 1942791649 | 19.800 | 263.993 | 10.032 | 0.010 |
| Organic Cherry Flavor #652865 | Gold Coast | Dec. 2, 2016 | 1.650 | 21.999 | 0.836 | 0.001 |
| All Natural Strawberry Flavor #34775 | Virginia Dare | S79315 | 1.100 | 14.666 | 0.557 | 0.001 |
| All Natural Raspberry Flavor #26507 | Virginia Dare | S79313 | 1.650 | 21.999 | 0.836 | 0.001 |
| Edicol 60-70 (guar gum) | Lucid | 152/2016 | 0.250 | 3.333 | 0.127 | 0.000 |
| Sunflower Lecithin | Now | None on container | 0.500 | 6.667 | 0.253 | 0.000 |
| | | TOTAL | 100.000 | 1333.303 | 50.665 | 0.051 |

The blend process was as follows.
1. Screen Ibuprofen, Isomalt, and Xylitol through a #20 screen.
2. Screen flavor through a #40 and lecithin through a #40 screen.
3. Add the following into a plastic cup in the following order:
  a. Isomalt
  b. Ibuprofen
  c. Lecithin
  d. flavor
  e. Guar gum
  f Xylitol
4. Blend by rotating the plastic cup at a consistent pace for 3 minutes.
Results:
With 2.666 g dry sample swallowed, the flavor was intense and sweetness good with no bitterness and very little throat irritation which went away in about 3 minutes.
With 2.666 g sample in 1 tsp. water, sample dispersed easily to yield a pink cloudy dispersion. The flavor was intense with good sweetness with no bitterness and virtually no throat irritation.

Example 18

This example evaluated an agglomeration blending approach for Ibuprofen and Lecithin with 90:10 ratio of Ibuprofen to Lecithin.
Ibuprofen/Lecithin Agglomeration/Coating/Granulation formulation.

TABLE 18a

| % Solids in $H_2O$ | Batch Weight (g) | Total Coating (g) | % Lecithin in $H_2O$ | Total $H_2O$ (g) |
|---|---|---|---|---|
| 100.0 | 7.000 | 7.000 | 100.0 | 0.000 |

TABLE 18b

| Ingredient | Vendor | Lot Number | % in Granulation | g/batch size | kg/batch size |
|---|---|---|---|---|---|
| Ibuprofen, USP | SI group | 7050-3921 | 80.000 | 5.600 | 0.006 |
| Sunflower Lecithin | Now | None on container | 20.000 | 1.400 | 0.001 |
| TOTAL | | | 100.000 | 7.000 | 0.007 |

The following process was used.
1. Screen lecithin through #40 screen.
2. Screen Ibuprofen through #20 screen.
3. Blend lecithin and ibuprofen for 3 minutes.
4. Weigh water in Suitable container. Add incrementally with stirring until an agglomeration is achieved.
5. Dry at room temperature until thoroughly dry.
6. Screen granulation through a #40 screen.
Results.
Agglomeration tastes very bitter.so that blend with additional components was not made.

Example 19

This example evaluated an agglomeration blending approach for Ibuprofen and Lecithin with 50:50 ratio of Ibuprofen to Lecithin using a low quantity of water.
Ibuprofen/Lecithin Agglomeration/Coating/Granulation formulation.

TABLE 19a

| % Solids in $H_2O$ | Batch Weight (g) | Total Coating (g) | % Lecithin in $H_2O$ | Total $H_2O$ (g) |
|---|---|---|---|---|
| 100.00 | 14.000 | 14.000 | 100.0 | 0.000 |

TABLE 19b

| Ingredient | Vendor | Lot Number | % in Granulation | g/batch size | kg/batch size |
|---|---|---|---|---|---|
| Ibuprofen, USP | SI group | 7050-3921 | 50.000 | 7.000 | 0.007 |
| Sunflower Lecithin | Now | None on container | 50.000 | 7.000 | 0.007 |
| TOTAL | | | 100.000 | 14.000 | 0.014 |

The following process was used.
1. Screen lecithin through #40 screen.
2. Screen Ibuprofen through #20 screen.
3. Blend lecithin and ibuprofen for 3 minutes.
4. Weigh water in Suitable container. Add incrementally with stirring until an agglomeration is achieved (0.471 g $H_2O$).
5. Dry at room temperature until thoroughly dry.
6. Screen granulation.
Results:
400 mg agglomeration was swallowed dry with some bitterness and a little throat irritation detected.
Granules were too soft and no further blending was done.

Example 20

This example evaluated 7.5% formulation with Citric Acid at 0.5%, 0.25% and 0.125%.

TABLE 20a

| Bulk Blend. (IBU-20) | | | |
|---|---|---|---|
| Blend Fill Weight (mg) | API (mg) | Batch (units) | Batch Weight (g) |
| 1,333.3 | 100.0 | 38.0 | 50.665 |

TABLE 20b

| Bulk Blend. (IBU-20). | | | | | | |
|---|---|---|---|---|---|---|
| Ingredient | Vendor | Lot Number | % Concentration | mg/blend fill | g/batch size | kg/batch size |
| Ibuprofen, USP | SI group | 7050-3921 | 7.500 | 100.000 | 3.800 | 0.004 |

TABLE 20b-continued

Bulk Blend. (IBU-20).

| Ingredient | Vendor | Lot Number | % Concentration | mg/blend fill | g/batch size | kg/batch size |
|---|---|---|---|---|---|---|
| Isomalt (Galen IQ) | Beneo GMBH | L1216907U2 | 67.550 | 900.644 | 34.224 | 0.034 |
| Xylitol (Xivia CM170) | Dupont | 1942791649 | 19.800 | 263.993 | 10.032 | 0.010 |
| Organic Cherry Flavor #652865 | Gold Coast | Dec. 2, 2016 | 1.650 | 21.999 | 0.836 | 0.001 |
| All Natural Strawberry Flavor #34775 | Virginia Dare | S79315 | 1.100 | 14.666 | 0.557 | 0.001 |
| All Natural Raspberry Flavor #26507 | Virginia Dare | S79313 | 1.650 | 21.999 | 0.836 | 0.001 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| TOTAL | | | 100.000 | 1333.303 | 50.665 | 0.051 |

The following process was used.

1. Screen Ibuprofen, Isomalt, and Xylitol through a #20 screen.
2. Screen flavor through a #40 and lecithin through a #40 screen.
3. Add the following into a plastic cup in the following order:
   a. Isomalt
   b. Ibuprofen
   c. Lecithin
   d. flavor
   e. Guar gum
   f. Xylitol
4. Blend by rotating the plastic cup at a consistent pace for 3 minutes.

TABLE 20c

Citric Acid 0.5% (IBU-20-1).

| Blend Fill Weight (mg) | API (mg) | Batch (units) | Batch Weight (g) |
|---|---|---|---|
| 1,333.3 | 100.0 | 7.5 | 10.000 |

TABLE 20d

Citric Acid 0.5% (IBU-20-1).

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 0.750 | 0.001 |
| Isomalt (Galen IQ) | Beneo GMBH | L1216907U2 | 67.050 | 893.978 | 6.705 | 0.007 |
| Xylitol (Xivia CM170) | Dupont | 1942791649 | 19.800 | 263.993 | 1.980 | 0.002 |
| Organic Cherry Flavor #652865 | Gold Coast | Dec. 2, 2016 | 1.650 | 21.999 | 0.165 | 0.000 |
| All Natural Strawberry Flavor #34775 | Virginia Dare | S79315 | 1.100 | 14.666 | 0.110 | 0.000 |
| All Natural Raspberry Flavor #26507 | Virginia Dare | S79313 | 1.650 | 21.999 | 0.165 | 0.000 |

TABLE 20d-continued

| | | | Citric Acid 0.5% (IBU-20-1). | | | |
|---|---|---|---|---|---|---|
| Ingredient | Vendor | Lot Number | % Concentration | mg/blend fill | g/batch size | kg/batch size |
| Edicol 60-70 (guar gum) | Lucid | 152/2016 | 0.250 | 3.333 | 0.025 | 0.000 |
| Lipoid H 20 Sunflower Lecithin | Lipoid GMBH | 536900-2160013 | 0.500 | 6.667 | 0.050 | 0.000 |
| Citric Acid | Anthony's Almonds | May 16, 2019 | 0.500 | 6.667 | 0.050 | 0.000 |
| | TOTAL | | 100.000 | 1333.303 | 10.000 | 0.010 |

TABLE 20e

| Citric Acid at 0.25% (IBU-20-2). | | | |
|---|---|---|---|
| Blend Fill Weight (mg) | API (mg) | Batch (units) | Batch Weight (g) |
| 1,333.3 | 100.0 | 7.5 | 10.000 |

TABLE 20f

| | | | Citric Acid at 0.25% (IBU-20-2) | | | |
|---|---|---|---|---|---|---|
| Ingredient | Vendor | Lot Number | % Concentration | mg/blend fill | g/batch size | kg/batch size |
| Ibuprofen, USP | SI group | 7050-3921 | 7.500 | 100.000 | 0.750 | 0.001 |
| Isomalt (Galen IQ) | Beneo GMBH | L1216907U2 | 67.300 | 897.311 | 6.730 | 0.007 |
| Xylitol (Xivia CM170) | Dupont | 1942791649 | 19.800 | 263.993 | 1.980 | 0.002 |
| Organic Cherry Flavor #652865 | Gold Coast | 12/2/2016 | 1.650 | 21.999 | 0.165 | 0.000 |
| All Natural Strawberry Flavor #34775 | Virginia Dare | S79315 | 1.100 | 14.666 | 0.110 | 0.000 |
| All Natural Raspberry Flavor #26507 | Virginia Dare | S79313 | 1.650 | 21.999 | 0.165 | 0.000 |
| Edicol 60-70 (guar gum) | Lucid | 152/2016 | 0.250 | 3.333 | 0.025 | 0.000 |
| Lipoid H 20 Sunflower Lecithin | Lipoid GMBH | 536900-2160013 | 0.500 | 6.667 | 0.050 | 0.000 |
| Citric Acid | Anthony's Almonds | 5/16/2019 | 0.250 | 3.333 | 0.025 | 0.000 |
| | TOTAL | | 100.000 | 1333.303 | 10.000 | 0.010 |

TABLE 20g

| Citric Acid at 0.125% (IBU-20-3). | | | |
|---|---|---|---|
| Blend Fill Weight (mg) | API (mg) | Batch (units) | Batch Weight (g) |
| 1,333.3 | 100.0 | 7.5 | 10.000 |

TABLE 20h

Citric Acid at 0.125%(IBU-20-3).

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 0.750 | 0.001 |
| Isomalt (Galen IQ) | Beneo GMBH | L1216907U2 | 67.425 | 898.978 | 6.742 | 0.007 |
| Xylitol (Xivia CM170) | Dupont | 1942791649 | 19.800 | 263.993 | 1.980 | 0.002 |
| Organic Cherry Flavor #652865 | Gold Coast | 12/2/2016 | 1.650 | 21.999 | 0.165 | 0.000 |
| All Natural Strawberry Flavor #34775 | Virginia Dare | S79315 | 1.100 | 14.666 | 0.110 | 0.000 |
| All Natural Raspberry Flavor #26507 | Virginia Dare | S79313 | 1.650 | 21.999 | 0.165 | 0.000 |
| Edicol 60-70 (guar gum) | Lucid | 152/2016 | 0.250 | 3.333 | 0.025 | 0.000 |
| Lipoid H 20 Sunflower Lecithin | Lipoid GMBH | 536900-2160013 | 0.500 | 6.667 | 0.050 | 0.000 |
| Citric Acid | Anthony's Almonds | 5/16/2019 | 0.125 | 1.667 | 0.012 | 0.000 |
| TOTAL | | | 100.000 | 1333.303 | 10.000 | 0.010 |

The blending process was as follows.
1. Weigh a 10 g portion of the bulk blend.
2. Screen Citric Acid through a #40 screen.
3. Blend citric acid with the bulk blend for 1 minute.

TABLE 20i

Citric Acid at 0.125% and increased flavorings (IBU-20-4).

| Blend Fill Weight (mg) | API (mg) | Batch (units) | Batch Weight (g) |
|---|---|---|---|
| 1,356.2 | 100.0 | 7.5 | 10.172 |

TABLE 20j

Citric Acid at 0.125% and increased flavorings (IBU-20-4).

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.374 | 100.000 | 0.750 | 0.001 |
| Isomalt (Galen IQ) | Beneo GMBH | L1216907U2 | 65.951 | 894.427 | 6.708 | 0.007 |
| Xylitol (Xivia CM170) | Dupont | 1942791649 | 19.800 | 268.528 | 2.014 | 0.002 |
| Organic Cherry Flavor #652865 | Gold Coast | 12/2/2016 | 2.000 | 27.124 | 0.203 | 0.000 |
| All Natural Strawberry Flavor #34775 | Virginia Dare | S79315 | 2.000 | 27.124 | 0.203 | 0.000 |
| All Natural Raspberry Flavor #26507 | Virginia Dare | S79313 | 2.000 | 27.124 | 0.203 | 0.000 |
| Edicol 60-70 (guar gum) | Lucid | 152/2016 | 0.250 | 3.391 | 0.025 | 0.000 |
| Lipoid H 20 Sunflower Lecithin | Lipoid GMBH | 536900-2160013 | 0.500 | 6.781 | 0.051 | 0.000 |
| Citric Acid | Anthony's Almonds | 5/16/2019 | 0.125 | 1.695 | 0.013 | 0.000 |
| TOTAL | | | 100.000 | 1356.194 | 10.171 | 0.010 |

The Blend process was as follows.
1. Weigh a 10 g portion of the bulk blend.
2. Screen flavors through a #40 and add the difference.
Cherry: 0.035
Strawberry: 0.09
Raspberry: 0.035
3. Screen Citric Acid through a #40 screen.
4. Blend Flavors and Citric Acid for 1 minute.
TOTAL Weight=10.172 g
Results:
Citric Acid from 0.5-0.25% was too sour.
Citric Acid at 0.125% (IBU-020-3) lessens the sour flavor but does bring out the fruit complex.
IBU-20-4:
With 2.712 g dry sample, flavor was very intense with a little spice note. Sample was not sour, but brought out a little bit of tartness. Although not swallowed; there was a little bit of throat irritation.

With 2.712 g sample in 1 tsp water, swallowed, flavor and sweetness were excellent with no bitterness or throat irritation.

Example 21

This example repeats the IBU-020-4 formulation in Example 29 at a 50 g batch weight.

TABLE 21a

| | Citric Acid at 0.125% | | |
|---|---|---|---|
| Blend Fill Weight (mg) | API (mg) | Batch (units) | Batch Weight (g) |
| 1,333.3 | 100.0 | 38.0 | 50.665 |

TABLE 21b

| | | | Citric Acid at 0.125%, | | | |
|---|---|---|---|---|---|---|
| Ingredient | Vendor | Lot Number | % Concentration | mg/blend fill | g/batch size | kg/batch size |
| Ibuprofen, USP | SI group | 7050-3921 | 7.500 | 100.000 | 3.800 | 0.004 |
| Isomalt (Galen IQ) | Beneo GMBH | L1216907U2 | 65.825 | 877.645 | 33.350 | 0.033 |
| Xylitol (Xivia CM170) | Dupont | 1942791649 | 19.800 | 263.993 | 10.032 | 0.010 |
| Organic Cherry Flavor #652865 | Gold Coast | 12/2/2016 | 2.000 | 26.666 | 1.013 | 0.001 |
| All Natural Strawberry Flavor #34775 | Virginia Dare | S79315 | 2.000 | 26.666 | 1.013 | 0.001 |
| All Natural Raspberry Flavor #26507 | Virginia Dare | S79313 | 2.000 | 26.666 | 1.013 | 0.001 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| Citric Acid Almonds | Anthony's | 5/16/2019 | 0.125 | 1.667 | 0.063 | 0.000 |
| | TOTAL | | 100.000 | 1333.303 | 50.665 | 0.051 |

The blend process was as follows.

1. Screen Ibuprofen, Isomalt, and Xylitol through a #20 screen.
2. Screen flavor and citric acid through a #40 and lecithin through a #40 screen.
3. Add the following into a plastic cup in the following order:
   a. Isomalt
   b. Ibuprofen
   c. Lecithin
   d. Flavors
   e. Citric acid
   e. Guar gum
   f. Xylitol
4. Blend by rotating the plastic cup at a consistent pace for 3 minutes.

Results:

With 2.666 g dry sample, swallow flavor and sweetness were excellent with no bitterness and very little throat irritation.

With 2.666 g sample in 1 tsp. water, swallowed, flavor and sweetness were excellent with no bitterness and no throat irritation.

Example 22

This example evaluated the formula in example 21, but with a 25% reduction in flavor components.

TABLE 22a

| Blend Fill Weight (mg) | API (mg) | Batch (units) | Batch Weight (g) |
|---|---|---|---|
| 1,333.3 | 100.0 | 38.0 | 50.665 |

TABLE 22b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 67.325 | 897.644 | 34.110 | 0.034 |
| Xylitol (Xivia CM170) | Dupont | 1942791649 | 19.800 | 263.993 | 10.032 | 0.010 |
| Organic Cherry Flavor #652865 | Gold Coast | 12/2/2016 | 1.500 | 20.000 | 0.760 | 0.001 |
| All Natural Strawberry Flavor #34775 | Virginia Dare | S79315 | 1.500 | 20.000 | 0.760 | 0.001 |
| All Natural Raspberry Flavor #26507 | Virginia Dare | S79313 | 1.500 | 20.000 | 0.760 | 0.001 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| Citric Acid | Anthony's Almonds | 5/16/2019 | 0.125 | 1.667 | 0.063 | 0.000 |
| TOTAL | | | 100.000 | 1333.303 | 50.665 | 0.051 |

The blend Process was as follows.
1. Screen Ibuprofen, Isomalt, and Xylitol through a #20 screen.
2. Screen flavor and citric acid through a #40 and lecithin through a #40 screen.
3. Add the following into a plastic cup in the following order:
a. Isomalt
b. Ibuprofen
c. Lecithin
d. Flavors
e. Citric acid
e. Guar gum
f. Xylitol
4. Blend by rotating the plastic cup at a consistent pace for 3 minutes.

Results:

With 2.666 g dry sample, swallowed, flavor intensity and sweetness were good with light spicy flavor, no bitterness and little throat irritation.

With 2.666 g sample 1 tsp. water, flavor intensity and sweetness were good with no bitterness and no throat irritation.

Example 23

This example evaluated a formulation with reduced flavor components (33% reduction compared to example 22).

TABLE 23a

| Blend Fill Weight (mg) | API (mg) | Batch (units) | Batch Weight (g) |
|---|---|---|---|
| 1,333.3 | 100.0 | 38.0 | 50.665 |

TABLE 23b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 68.825 | 917.644 | 34.870 | 0.035 |
| Xylitol (Xivia CM170) | Dupont | 1942791649 | 19.800 | 263.993 | 10.032 | 0.010 |
| Organic Cherry Flavor #652865 | Gold Coast | 12/2/2016 | 1.000 | 13.333 | 0.507 | 0.001 |
| All Natural Strawberry Flavor #34775 | Virginia Dare | S79315 | 1.000 | 13.333 | 0.507 | 0.001 |
| All Natural Raspberry Flavor #26507 | Virginia Dare | S79313 | 1.000 | 13.333 | 0.507 | 0.001 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| Citric Acid | Anthony's Almonds | 5/16/2019 | 0.125 | 1.667 | 0.063 | 0.000 |
| TOTAL | | | 100.000 | 1333.303 | 50.665 | 0.051 |

The blend process was as follows.
1. Screen Ibuprofen, Isomalt, and Xylitol through a #20 screen.
2. Screen flavor and citric acid through a #40 and lecithin through a #40 screen.
3. Add the following into a plastic cup in the following order:
   a. Isomalt
   b. Ibuprofen
   c. Lecithin
   d. Flavors
   e. Citric acid
   e. Guar gum
   f. Xylitol
4. Blend by rotating the plastic cup at a consistent pace for 3 minutes.

Results:

With 2.666 g dry sample, swallowed, flavor intensity and sweetness were good with no bitterness and little throat irritation With 2.666 g sample in 1 tsp. water, flavor intensity and sweetness were good with no bitterness and no throat irritation.

Example 24

This example evaluated a formulation with a change in Cherry flavoring supplier from GC to VC.

TABLE 24a

| Blend Fill Weight (mg) | API (mg) | Batch (units) | Batch Weight (g) |
|---|---|---|---|
| 1,333.3 | 100.0 | 38.0 | 50.665 |

TABLE 25b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 68.825 | 917.644 | 34.870 | 0.035 |
| Xylitol (Xivia CM170) | Dupont | 1942791649 | 19.800 | 263.993 | 10.032 | 0.010 |
| All Natural Cherry Flavor #34327 | Virginia Dare | S79579 | 1.000 | 13.333 | 0.507 | 0.001 |
| All Natural Strawberry Flavor #34775 | Virginia Dare | S79315 | 1.000 | 13.333 | 0.507 | 0.001 |
| All Natural Raspberry Flavor #26507 | Virginia Dare | S79313 | 1.000 | 13.333 | 0.507 | 0.001 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| Citric Acid | Anthony's Almonds | 5/16/2019 | 0.125 | 1.667 | 0.063 | 0.000 |
| TOTAL | | | 100.000 | 1333.303 | 50.665 | 0.051 |

The blend process was as follows.
1. Screen Ibuprofen, Isomalt, and Xylitol through a #20 screen.
2. Screen flavor and citric acid through a #40 and lecithin through a #40 screen.
3. Add the following into a plastic cup in the following order:
   a. Isomalt
   b. Ibuprofen
   c. Lecithin
   d. Flavors
   e. Citric acid
   e. Guar gum
   f. Xylitol
4. Blend by rotating the plastic cup at a consistent pace for 3 minutes.

Results:

With 2.666 g dry sample swallowed, flavor and sweetness were excellent with no bitterness and very little throat irritation.

With 2.666 g sample in 1 tsp. water, flavor and sweetness were excellent with no bitterness and no throat irritation. Overall the VD Cherry flavor is equal or superior to the GC cherry.

Example 25

This example evaluated a change from VD raspberry (color) to VD raspberry (colorless). Otherwise all conditions were the same as in example 24.

TABLE 25a

| Blend Fill Weight (mg) | API (mg) | Batch (units) | Batch Weight (g) |
|---|---|---|---|
| 1,333.3 | 100.0 | 38.0 | 50.665 |

TABLE 25b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 68.825 | 917.644 | 34.870 | 0.035 |
| Xylitol (Xivia CM170) | Dupont | 1942791649 | 19.800 | 263.993 | 10.032 | 0.010 |
| All Natural Cherry Flavor #34327 | Virginia Dare | S79579 | 1.000 | 13.333 | 0.507 | 0.001 |
| All Natural Strawberry Flavor #34775 | Virginia Dare | S79315 | 1.000 | 13.333 | 0.507 | 0.001 |
| All Natural Raspberry Flavor #20625 | Virginia Dare | S79313 | 1.000 | 13.333 | 0.507 | 0.001 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| Citric Acid | Anthony's Almonds | 5/16/2019 | 0.125 | 1.667 | 0.063 | 0.000 |
| TOTAL | | | 100.000 | 1333.303 | 50.665 | 0.051 |

The blend process was as follows.
1. Screen Ibuprofen, Isomalt, and Xylitol through a #20 screen.
2. Screen flavor and citric acid through a #40 and lecithin through a #40 screen.
3. Add the following into a plastic cup in the following order:
  a. Isomalt
  b. Ibuprofen
  c. Lecithin
  d. Flavors
  e. Citric acid
  e. Guar gum
  f. Xylitol
4. Blend by rotating the plastic cup at a consistent pace for 3 minutes.

Results:
With 2.666 g dry sample, the raspberry flavor was too strong with a volatile essence.

Example 26

This example evaluated a formulation with VD Raspberry (colorless) in an amount (0.5%).

TABLE 26a

| Blend Fill Weight (mg) | API (mg) | Batch (units) | Batch Weight (g) |
|---|---|---|---|
| 1,333.3 | 100.0 | 38.0 | 50.665 |

TABLE 26b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 69.325 | 924.310 | 35.124 | 0.035 |
| Xylitol (Xivia CM170) | Dupont | 1942791649 | 19.800 | 263.993 | 10.032 | 0.010 |
| All Natural Cherry Flavor #34327 | Virginia Dare | S79579 | 1.000 | 13.333 | 0.507 | 0.001 |
| All Natural Strawberry Flavor #34775 | Virginia Dare | S79315 | 1.000 | 13.333 | 0.507 | 0.001 |
| All Natural Raspberry Flavor #20625 | Virginia Dare | S79577 | 0.500 | 6.667 | 0.253 | 0.000 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| Citric Acid | Anthony's Almonds | 5/16/2019 | 0.125 | 1.667 | 0.063 | 0.000 |
| | TOTAL | | 100.000 | 1333.303 | 50.665 | 0.051 |

The blend process was as follows.
1. Screen Ibuprofen, Isomalt, and Xylitol through a #20 screen.
2. Screen flavor and citric acid through a #40 and lecithin through a #40 screen.
3. Add the following into a plastic cup in the following order:
a. Isomalt
b. Ibuprofen
c. Lecithin
d. Flavors
e. Citric acid
e. Guar gum
f. Xylitol
4. Blend by rotating the plastic cup at a consistent pace for 3 minutes.

Results:
With 2.666 g dry sample, swallowed, flavor was much improved with the raspberry much less overwhelming over the other flavors compared to example 25 and with a little bit of volatile essence through the nose.

Example 27

This example evaluated a formulation with VD Raspberry (colorless) in an amount (0.25%).

TABLE 27a

| Blend Fill Weight (mg) | API (mg) | Batch (units) | Batch Weight (g) |
|---|---|---|---|
| 1,333.3 | 100.0 | 38.0 | 50.665 |

TABLE 27b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 69.575 | 927.643 | 35.250 | 0.035 |
| Xylitol (Xivia CM170) | Dupont | 1942791649 | 19.800 | 263.993 | 10.032 | 0.010 |
| All Natural Cherry Flavor #34327 | Virginia Dare | S79579 | 1.000 | 13.333 | 0.507 | 0.001 |
| All Natural Strawberry Flavor #34775 | Virginia Dare | S79315 | 1.000 | 13.333 | 0.507 | 0.001 |
| All Natural Raspberry Flavor #20625 | Virginia Dare | S79577 | 0.250 | 3.333 | 0.127 | 0.000 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| Citric Acid | Anthony's Almonds | 5/16/2019 | 0.125 | 1.667 | 0.063 | 0.000 |
| | TOTAL | | 100.000 | 1333.303 | 50.665 | 0.051 |

The blend process was as follows.
1. Screen Ibuprofen, Isomalt, and Xylitol through a #20 screen.
2. Screen flavor and citric acid through a #40 and lecithin through a #40 screen.
3. Add the following into a plastic cup in the following order:
   a. Isomalt
   b. Ibuprofen
   c. Lecithin
   d. Flavors
   e. Citric acid
   e. Guar gum
   f. Xylitol
4. Blend by rotating the plastic cup at a consistent pace for 3 minutes.

Results:

With 2.666 g dry sample, swallowed, raspberry flavor was a little too intense with spice note and no volatile essence or bitterness and little throat irritation.

Example 28

This example evaluated a formulation with VD Raspberry (colorless) in an amount of 0.1%.

TABLE 28a

| Blend Fill Weight (mg) | API (mg) | Batch (units) | Batch Weight (g) |
|---|---|---|---|
| 1,333.3 | 100.0 | 38.0 | 50.665 |

TABLE 28b

| Ingredient | Vendor | Lot Number | % Concentration | mg/blend fill | g/batch size | kg/batch size |
|---|---|---|---|---|---|---|
| Ibuprofen, USP | SI group | 7050-3921 | 7.500 | 100.000 | 3.800 | 0.004 |
| Isomalt (Galen IQ) | Beneo GMBH | L1216907U2 | 69.725 | 929.643 | 35.326 | 0.035 |
| Xylitol (Xivia CM170) | Dupont | 1942791649 | 19.800 | 263.993 | 10.032 | 0.010 |
| All Natural Cherry Flavor #34327 | Virginia Dare | S79579 | 1.000 | 13.333 | 0.507 | 0.001 |
| All Natural Strawberry Flavor #34775 | Virginia Dare | S79315 | 1.000 | 13.333 | 0.507 | 0.001 |
| All Natural Raspberry Flavor #20625 | Virginia Dare | S79577 | 0.100 | 1.333 | 0.051 | 0.000 |
| Edicol 60-70 (guar gum) | Lucid | 152/2016 | 0.250 | 3.333 | 0.127 | 0.000 |
| Lipoid H 20 Sunflower Lecithin | Lipoid GMBH | 536900-2160013 | 0.500 | 6.667 | 0.253 | 0.000 |
| Citric Acid | Anthony's Almonds | 5/16/2019 | 0.125 | 1.667 | 0.063 | 0.000 |
| | TOTAL | | 100.000 | 1333.303 | 50.665 | 0.051 |

The blend process was as follows.
1. Screen Ibuprofen, Isomalt, and Xylitol through a #20 screen.
2. Screen flavor and citric acid through a #40 and lecithin through a #40 screen.
3. Add the following into a plastic cup in the following order:
   a. Isomalt
   b. Ibuprofen
   c. Lecithin
   d. Flavors
   e. Citric acid
   e. Guar gum
   f. Xylitol
4. Blend by rotating the plastic cup at a consistent pace for 3 minutes.

Results:

With 2.666 g dry sample swallowed, flavor intensity was at the right level, but Raspberry was still dominating other flavors with no bitterness and little throat irritation With 2.666 g sample in 1 tsp. water and no swallowing, flavor intensity was good.

Example 29

This example evaluated an ibuprofen powder blend compacted into a tablet. This is from the same formula as example 28 with the addition of 1% Magnesium Stearate added as a lubricant. The target weight of 1.333 g of powder contains a target dose of 100 mg of ibuprofen. Tablets were compressed on a rotary tablet press.

TABLE 29a

| Avg. Applied Force (kN) | Tablet Weight (g) | | | | | | Statistics | |
|---|---|---|---|---|---|---|---|---|
| | No. 1 | No. 2 | No. 3 | No. 4 | No.5 | No. 6 | Avg. | % RSD |
| 3.68 | 1.336 | 1.340 | 1.338 | 1.33 | 1.325 | 1.327 | 1.333 | 0.4 |
| 4.64 | 1.325 | 1.321 | 1.33 | 1.322 | 1.338 | 1.337 | 1.329 | 0.5 |
| 5.50 | 1.322 | 1.329 | 1.331 | 1.333 | 1.338 | 1.328 | 1.330 | 0.4 |
| 7.00 | 1.335 | 1.329 | 1.338 | 1.332 | 1.331 | 1.325 | 1.332 | 0.3 |
| 8.16 | 1.338 | 1.341 | 1.336 | 1.337 | 1.342 | 1.344 | 1.340 | 0.2 |
| 9.24 | 1.344 | 1.358 | 1.355 | 1.346 | 1.348 | 1.344 | 1.349 | 0.4 |
| 11.18 | 1.364 | 1.360 | 1.364 | 1.350 | 1.348 | 1.370 | 1.359 | 0.6 |

TABLE 29b

| Avg. Applied Force (kN) | Tablet Thickness (mm) | | | | | | | Statistics |
|---|---|---|---|---|---|---|---|---|
| | No. 1 | No. 2 | No. 3 | No. 4 | No.5 | No. 6 | Avg. | % RSD |
| 3.68 | 5.72 | 5.68 | 5.67 | 5.65 | 5.62 | 5.59 | 5.66 | 0.7 |
| 4.64 | 5.48 | 5.47 | 5.48 | 5.49 | 5.48 | 5.47 | 5.48 | 0.1 |
| 5.50 | 5.34 | 5.44 | 5.40 | 5.35 | 5.35 | 5.36 | 5.37 | 0.7 |
| 7.00 | 5.23 | 5.15 | 5.16 | 5.17 | 5.23 | 5.23 | 5.20 | 0.7 |
| 8.16 | 5.12 | 5.07 | 5.08 | 5.08 | 5.09 | 5.08 | 5.09 | 0.3 |
| 9.24 | 4.98 | 5.02 | 4.98 | 4.96 | 4.94 | 4.91 | 4.97 | 0.7 |
| 11.18 | 4.86 | 4.84 | 4.85 | 4.87 | 4.86 | 4.90 | 4.86 | 0.4 |

TABLE 29c

| Avg. Applied Force (kN) | Diametrical Breaking Force (N) | | | | | | | Statistics |
|---|---|---|---|---|---|---|---|---|
| | No. 1 | No. 2 | No. 3 | No. 4 | No. 5 | No. 6 | Avg. | % RSD |
| 3.68 | 11 | 16 | 14 | 14 | 15 | 16 | 14 | 11.9 |
| 4.64 | 18 | 16 | 19 | 17 | 18 | 17 | 18 | 5.5 |
| 5.50 | 19 | 22 | 24 | 21 | 20 | 25 | 22 | 9.7 |
| 7.00 | 30 | 31 | 31 | 27 | 30 | 30 | 30 | 4.5 |
| 8.16 | 35 | 39 | 38 | 36 | 34 | 38 | 37 | 4.9 |
| 9.24 | 44 | 34 | 44 | 43 | 43 | 45 | 42 | 8.8 |
| 11.18 | 51 | 51 | 52 | 48 | 48 | 51 | 50 | 3.1 |

TABLE 29d

| Avg. Applied Force (kN) | Diametrical Breaking Force (kp) | | | | | | | Statistics |
|---|---|---|---|---|---|---|---|---|
| | No. 1 | No. 2 | No. 3 | No. 4 | No. 5 | No. 6 | Avg. | %RSD |
| 3.68 | 1.1 | 1.6 | 1.4 | 1.4 | 1.5 | 1.6 | 1.5 | 11.9 |
| 4.64 | 1.8 | 1.6 | 1.9 | 1.7 | 1.8 | 1.7 | 1.8 | 5.5 |
| 5.50 | 1.9 | 2.2 | 2.4 | 2.1 | 2.0 | 2.5 | 2.2 | 9.7 |
| 7.00 | 3.1 | 3.2 | 3.2 | 2.8 | 3.1 | 3.1 | 3.0 | 4.5 |
| 8.16 | 3.6 | 4.0 | 3.9 | 3.7 | 3.5 | 3.9 | 3.7 | 4.9 |
| 9.24 | 4.5 | 3.5 | 4.5 | 4.4 | 4.4 | 4.6 | 4.3 | 8.8 |
| 11.18 | 5.2 | 5.2 | 5.3 | 4.9 | 4.9 | 5.2 | 5.1 | 3.1 |

The Ibuprofen powder blend was compacted using the following tablet tooling: 18 mm round, flat-face tooling according to Table 29A. The resultant thicknesses of the compacted tablets are provided in Table 29B, and the diametrical breaking forces of the resultant tablets are provided in Tables 29C and 29D.

The data demonstrates that chewable, swallowable and/or orally disintegrating tablets can be produced with good weight control, acceptable thickness and breaking force.

This formula with the magnesium stearate is functional for the dry powder dosage form, suspension dosage form and the chewable tablet. Those of skill in the art will recognize the other lubricants including but not limited to stearic acid, calcium stearate, sodium stearate, sodium stearyl fumarate (PRUV®), talc, and hydrogenated soybean oil (STEROTEX®) can be used in the formula.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Publications incorporated herein by reference in their entirety include:
1. Sabaté E. Adherence to Long Term Therapies: Evidence for Action. World Health Organization. 2003. Available at: http://apps.who.int/medicinedocs/pdf/s4883e/s4883e.pdf.
2. Fass R., et al., Pharmacokinetic comparison of orally-disintegrating metoclopramide with conventional metoclopramide tablet formulation in healthy volunteers, (2009) *Aliment Pharmacol Ther* 30, 301-306.
3. Mennella, J A et al., The Bad Taste of Medicines: Overview of Basic Research on Bitter Taste, *Clin Ther* (2013) 35:1225-1246.
4. Walsh, J et al., Playing hide and seek with poorly tasting paediatric medicines: Do not forget the excipients, *Advanced Drug Delivery Reviews* (2014) 73: 14-33.
5. Kanabar, D. J., A clinical and safety review of paracetamol and ibuprofen in children, *Inflammopharmacol* (2017) 25:1-9; 6.
6. Kelley, B. P., Ibuprofen does not increase bleeding risk in plastic surgery: a systematic review and meta-analysis, *Plast Reconstr Surg*, (2016) 137:1309-1316.
7. Khalifa, N., et al., Use of ibuprofen sustained release for treating osteoarthritic pain: findings from 15 general medical practices in Egypt, *Rheumatology: Research and Reviews* (2014) 6:49-56.
8. de Klerk E., Patient compliance in rheumatoid arthritis, polymyalgia rheumatica, and gout, *J Rheumatol*, (2003) 30:44-54.
9. Rainsford K D, Ibuprofen: pharmacology, efficacy and safety, *Inflammopharmacology*. (2009) 7:275-342.
10. Rockwell W B and Ehrlich H P. Ibuprofen in acute-care therapy, *Ann Surg.* (1990) 211:78-83.
11. Shin et al., Pharmacokinetic and pharmacodynamic evaluation according to absorption differences in three formulations of ibuprofen, *Drug Des Devel Ther*. (2017) 11: 135-141.
12. Elworthy P H, et al., The Physical Chemistry of Lecithins, J Pharmacy Pharmacol (1956) 8: 1001-1018.

What is claimed is:

1. A free flowing dry powder oral formulation suitable for administration in each of an aqueous solution, aqueous dispersion, tablet, and powder dosage form,
wherein the formulation comprises an active pharmaceutical ingredient (API) in an amount from about 3% w/w to about 15% w/w, a surfactant or emulsifier in an amount from 0.1% w/w to 1% w/w, a galactomannan in an amount from about 0.05% w/w to about 0.5% w/w, one or more sweetening agents in an amount up to about 1.0% w/w, one or more diluents in an amount up to about 90% w/w, one or more flavoring agents in an amount from about 0.5% w/w to about 5% w/w and an organic acid in an amount from about 0.05% w/w to about 0.5% w/w, in a pharmaceutically acceptable preparation.

2. The formulation of claim 1, wherein the API is a non-steroidal anti-inflammatory drug (NSAID).

3. The formulation of claim 1, wherein the surfactant is an amphiphilic surfactant or emulsifier.

4. The formulation of claim 1, wherein the galactomannan comprises fenugreek gum, guar gum, tara gum, locust bean gum, or any combination thereof.

5. The formulation of claim 1, wherein the one or more diluents comprise isomalt, a dextrin, a maltodextrin, fructose, or any combination thereof.

6. The formulation of claim 1, wherein the one or more flavoring agents comprise fruity or mint flavoring agents.

7. A free flowing dry powder oral formulation suitable for administration in each of an aqueous solution, aqueous dispersion, tablet, and powder dosage form,
wherein the formulation comprises an active pharmaceutical ingredient (API) in an amount from about 3% w/w to about 15% w/w, a galactomannan in an amount from about 0.05% w/w to about 0.5% w/w, one or more sweetening agents in an amount up to about 90% w/w, two or more flavoring agents in an amount from about 0.5% w/w to about 5% w/w and an organic acid in an amount from about 0.05% w/w to about 0.5% w/w, in a pharmaceutically acceptable preparation.

8. The formulation of claim 7, wherein the API is a non-steroidal anti-inflammatory drug (NSAID).

9. The formulation of claim 7, wherein the galactomannan comprises fenugreek gum, guar gum, tara gum, locust bean gum, or any combination thereof.

10. The formulation of claim 7, wherein the galactomannan has a mannose to galactose ratio of from about 1:1 to about 4:1.

11. The formulation of claim 7, wherein the sweeting agent comprises isomalt.

12. The formulation of claim 7, wherein the two or more flavoring agents comprise fruity or mint flavoring agents.

13. The formulation of claim 12, wherein the fruity or mint flavoring agents are selected from cherry, strawberry, and raspberry.

14. The formulation of claim 13, wherein the surfactant or emulsifier is amphiphilic.

15. The formulation of claim 7, wherein the formulation solubility or dispersability in water is no more than about 0.5 w/v.

16. The formulation of claim 7, wherein the formulation is in a unit dosage container selected from the group consisting of a blister foil pack, stick pack, sachet, pouch, and bottle.

17. A free flowing dry powder oral formulation suitable for administration in each of an aqueous solution, aqueous dispersion, tablet, and powder dosage form,
wherein the formulation comprises a non-steroidal anti-inflammatory drug (NSAID) in an amount from about 6% w/w to about 10% w/w, a galactomannan in an amount from about 0.2% w/w to about 0.4% w/w, one or more sweetening agents in an amount up to about 90% w/w, one or more flavoring agents in an amount from about 0.5% w/w to about 5% w/w and an organic acid in an amount from about 0.1% w/w to about 0.2% w/w, in a pharmaceutically acceptable preparation.

18. The formulation of claim 17, wherein the NSAID comprises ibuprofen, the galactomannan comprises guar gum, the one or more sweetening agents comprise isomalt, and the organic acid comprises citric acid.

19. The formulation of claim 18, further comprising a surfactant or emulsifier in an amount from about 0.2% w/w to about 0.8% w/w.

20. The composition of claim 17, wherein the formulation solubility or dispersability in water is no more than about 0.5 w/v.

* * * * *